United States Patent [19]
Lin

[11] Patent Number: 5,813,324
[45] Date of Patent: Sep. 29, 1998

[54] NEEDLE DESTRUCTION DEVICE

[76] Inventor: A-Fang Lin, 58, Ma Yuan West St., Taichung, Taiwan

[21] Appl. No.: 965,656

[22] Filed: Nov. 6, 1997

[51] Int. Cl.⁶ .............................. B30B 3/04; B30B 9/00; B02C 9/04
[52] U.S. Cl. ..................... 100/91; 100/98 R; 100/161; 100/171; 100/172; 241/78; 241/159; 241/230; 241/606
[58] Field of Search .................. 100/91, 94, 98 R, 100/161, 171, 172, 176; 241/78, 159, 230, 606

[56] References Cited

U.S. PATENT DOCUMENTS

| | | | |
|---|---|---|---|
| 288,050 | 11/1883 | Gates | 241/159 |
| 744,567 | 11/1903 | Krusemark | 241/78 |
| 1,000,913 | 8/1911 | Hovendick | 241/230 |
| 1,075,781 | 10/1913 | Goldschmidt | 100/94 |
| 1,447,995 | 3/1923 | Mariani, Sr. | 241/159 |
| 2,087,806 | 7/1937 | McCune | 100/98 R |
| 2,417,599 | 3/1947 | Joyce, Jr. | 241/159 |
| 3,070,318 | 12/1962 | Blanchard | 241/78 |
| 3,749,004 | 7/1973 | Pagdin et al. | 100/94 |

FOREIGN PATENT DOCUMENTS

| | | | |
|---|---|---|---|
| 10504 | of 1902 | United Kingdom | 241/159 |
| 19590 | of 1908 | United Kingdom | 241/159 |
| 924806 | 5/1963 | United Kingdom | 100/98 R |

Primary Examiner—Stephen F. Gerrity

[57] ABSTRACT

A needle destruction device has a main frame, a lateral plate, a motor, a motor shaft extending from the motor, a drive gear connected to the motor shaft, a follower gear engaging with the drive gear, a first upper roller, a second upper roller, a first lower roller, a second lower roller, a first upper shaft extending from the first upper roller, a first upper driven gear connected to the first upper shaft, a second upper shaft extending from the second upper roller, a second upper driven gear connected to the second upper shaft, a first lower shaft extending from the first lower roller, a first lower driven gear connected to the first lower shaft, a second lower shaft extending from the second lower roller, a second lower driven gear connected to the second lower shaft, the first upper driven gear engaging with the follower gear and the second upper driven gear, the first lower driven gear engaging with the follower gear and the second lower driven gear.

2 Claims, 5 Drawing Sheets

NEEDLE DESTRUCTION DEVICE

BACKGROUND OF THE INVENTION

The present invention relates to a needle destruction device. More particularly, the present invention relates to a needle destruction device which can destroy a needle completely.

A conventional needle destruction device cannot destroy a needle completely. The user has to push a syringe into the conventional needle destruction device manually. The needle cannula may pierce the user. The needle is cut into a plurality of sections. However, a portion of the needle which remains in the needle hub cannot be cut into pieces. Because the conventional needle destruction device has only two rollers, the rollers do not have enough time to separate the syringe and the needle. The syringe and the needle pass through the spacing between the rollers very fast, so the portion of the needle remaining in the needle hub cannot be cut into pieces. The portion of the needle remaining in the needle hub may pierce the user.

SUMMARY OF THE INVENTION

An object of the present invention is to provide a needle destruction device which can destroy a needle completely.

Accordingly, a needle destruction device comprises a main frame, a lateral plate disposed on the main frame, a motor disposed on the main frame, a motor shaft extending from the motor, a drive gear connected to a first end of the motor shaft, a follower gear engaging with the drive gear, an upper guide plate disposed in the main frame, a lower guide plate disposed in the main frame and beneath the upper guide plate, an upper slot defined between the upper guide plate and the main frame, a lower slot defined between the lower guide plate and the main frame, a first block seat disposed on the upper guide plate, a first plug disposed on the lateral plate, a first spring disposed between the first block seat and the first plug, a first stud fastening the first plug on the lateral plate, a second block seat disposed on the upper guide plate, a second plug disposed on the lateral plate, a second spring disposed between the second block seat and the second plug, a second stud fastening the second plug on the lateral plate, a first upper roller disposed in the main frame, a second upper roller disposed in the main frame abutting the first upper roller, a first lower roller disposed in the main frame beneath the first upper roller, a second lower roller disposed in the main frame abutting the first lower roller and beneath the second upper roller, a first upper shaft extending from the first upper roller, a first upper driven gear connected to a first end of the first upper shaft, a second upper shaft extending from the second upper roller, a second upper driven gear connected to a first end of the second upper shaft, a first lower shaft extending from the first lower roller, a first lower driven gear connected to a first end of the first lower shaft, a second lower shaft extending from the second lower roller, a second lower driven gear connected to a first end of the second lower shaft, the first upper driven gear engaging with the follower gear, the second upper driven gear engaging with the first upper driven gear, the first lower driven gear engaging with the follower gear, and the second lower driven gear engaging with the first lower driven gear. A net is disposed between the first upper driven gear and the first lower driven gear and is disposed between the second upper driven gear and the second lower driven gear.

DETAILED DESCRIPTION OF THE INVENTION

Figure 3:
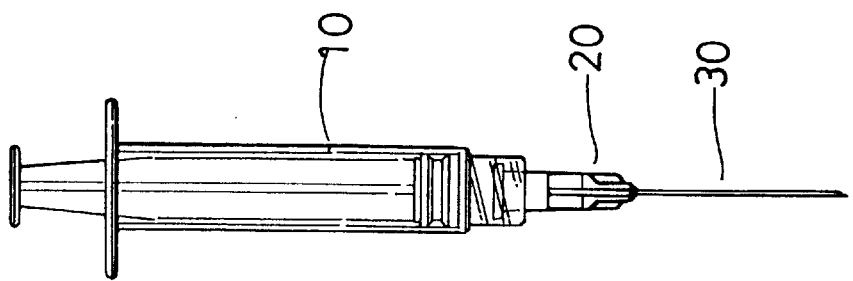
FIG. 3 is a perspective assembly view of a plastic syringe and a needle device without a needle sheath.
Figure 2:
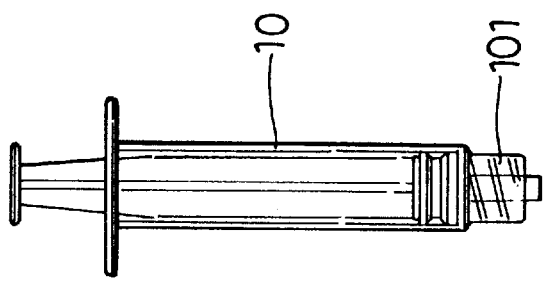
FIG. 2 is a perspective assembly view of a plastic syringe without a needle device and a needle sheath.
Figure 1:
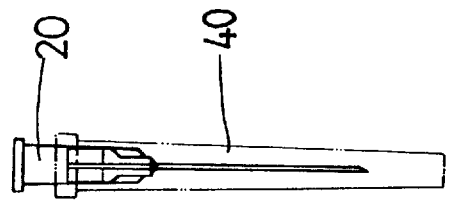
FIG. 1 is a perspective assembly view of a needle device and a needle sheath.
Figure 4:
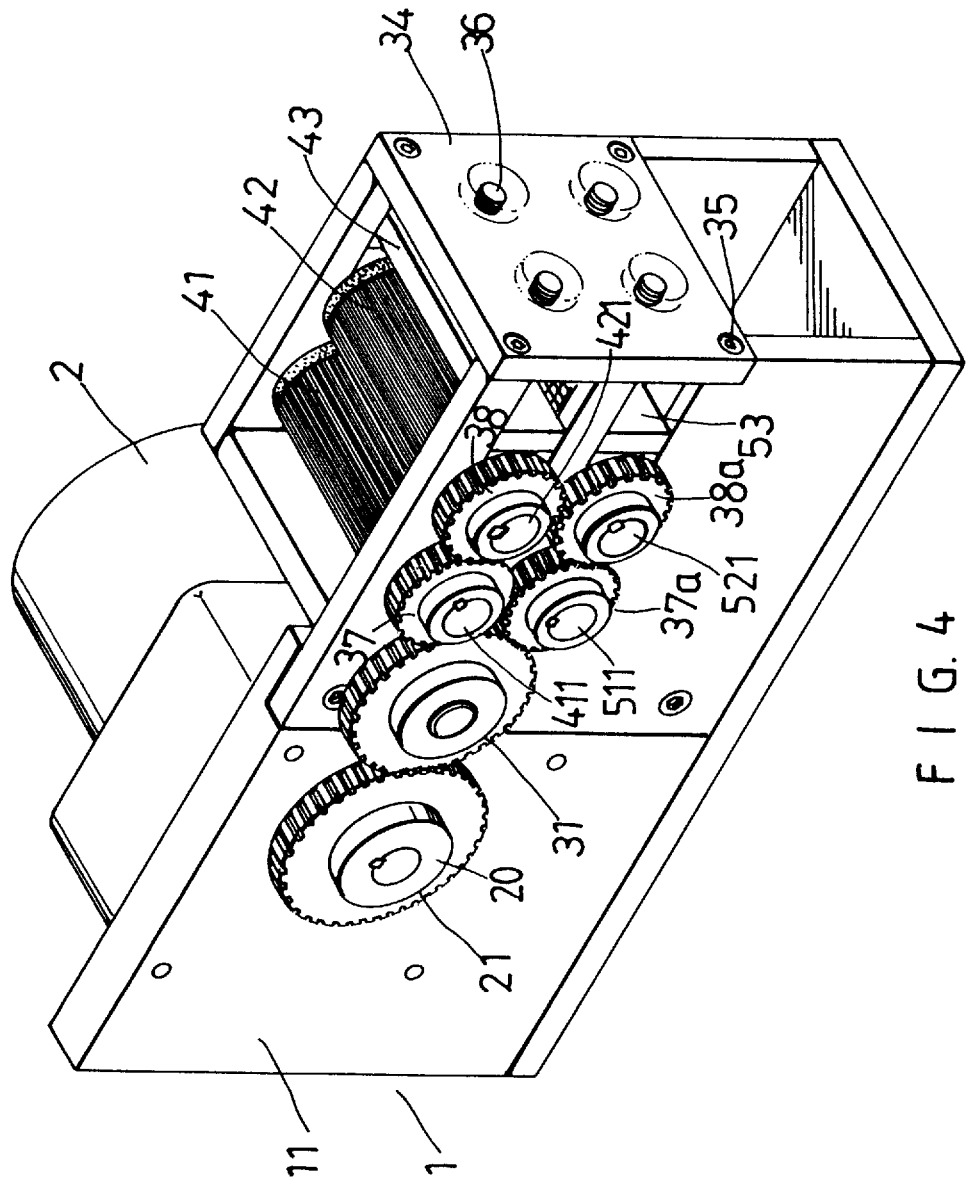
FIG. 4 is a perspective assembly view of a needle destruction device of a preferred embodiment in accordance with the present invention.
Figure 5:
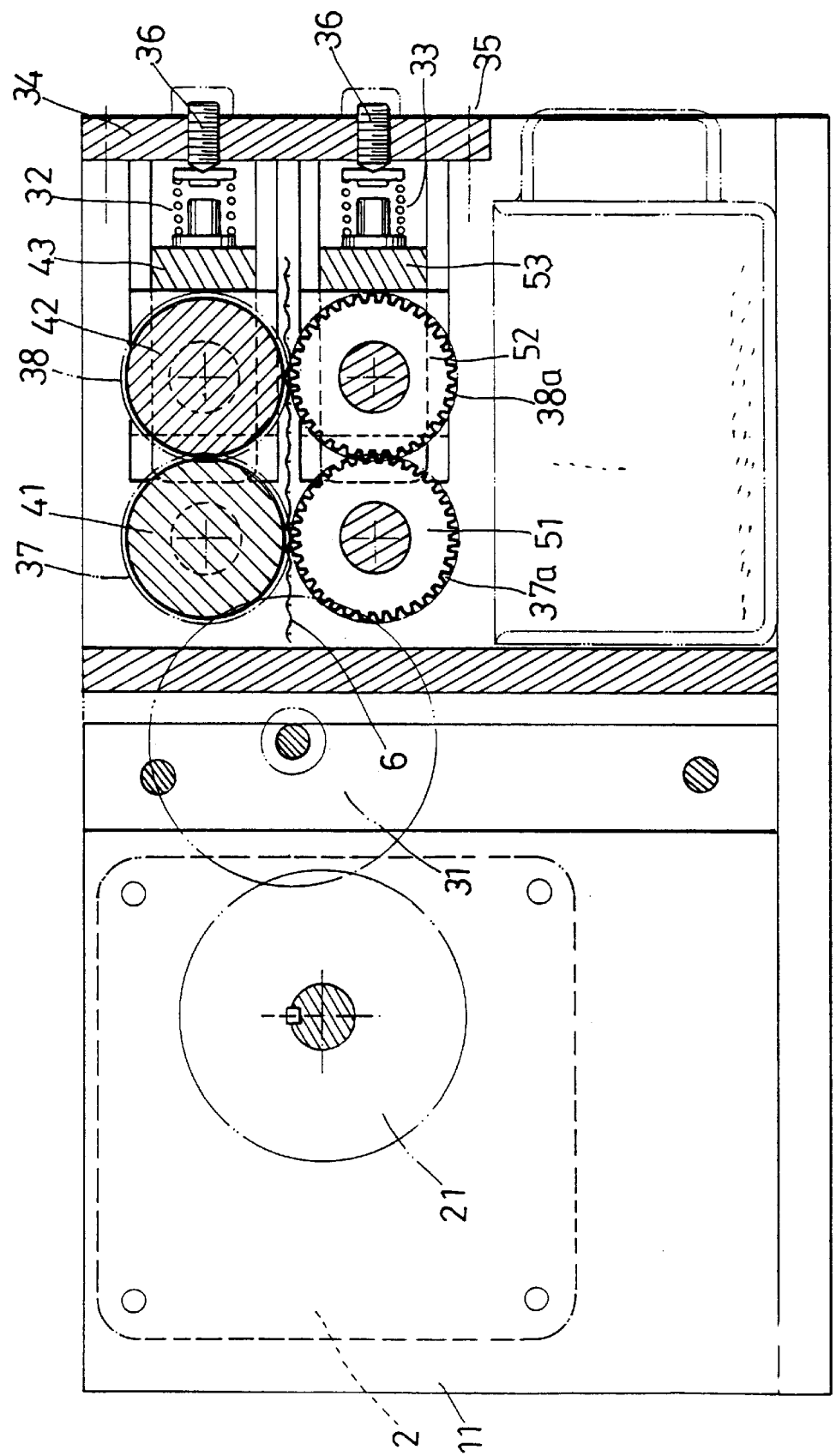
FIG. 5 is an elevational view of a needle destruction device of a preferred embodiment in accordance with the present invention.
Figure 6:
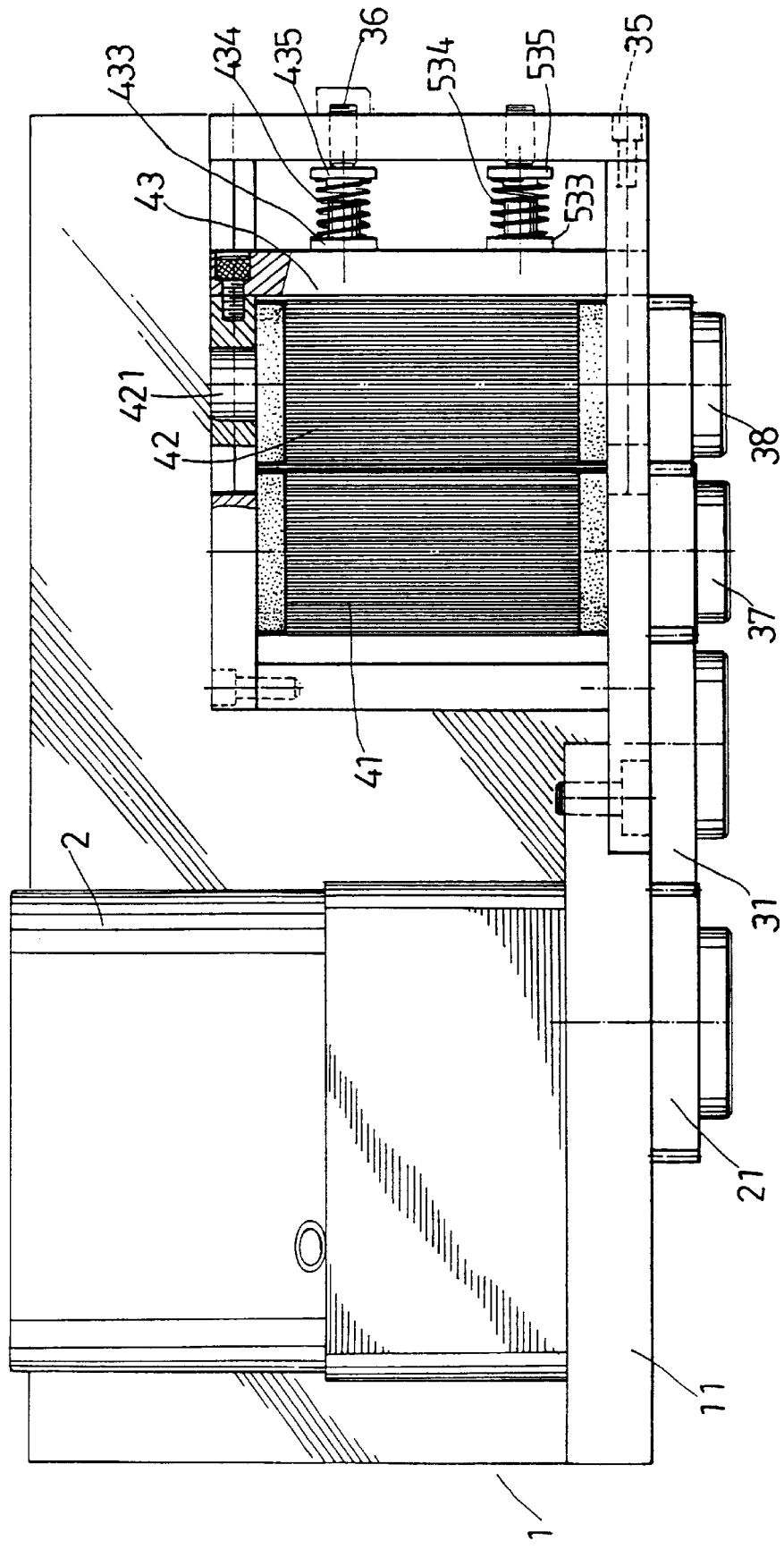
FIG. 6 is a top plan view of a needle destruction device of a preferred embodiment in accordance with the present invention.

Referring to FIGS. 1 to 3 first, a plastic syringe comprises a plastic barrel 10 and a needle device. The plastic barrel 10 has a locking tip 101. The needle device has a needle hub 20 and a needle cannula 30 inserted in the needle hub 20. The locking tip 101 encloses the rear portion of the needle hub 20. A needle sheath 40 covers the needle cannula 30, as shown in FIG. 1.

Referring to FIGS. 4 to 7, a needle destruction device 1 comprises a main frame 11, a lateral plate 34 disposed on the main frame 11, a motor 2 disposed on the main frame 11, a motor shaft 20 extending from the motor 2, a drive gear 21 connected to a first end of the motor shaft 20, a follower gear 31 engaging with the drive gear 21, an upper guide plate 43 disposed in the main frame 11, a lower guide plate 53 disposed in the main frame 11 and beneath the upper guide plate 43, an upper slot 32 defined between the upper guide plate 43 and the main frame 11, a lower slot 33 defined between the lower guide plate 53 and the main frame 11, a first block seat 433 disposed on the upper guide plate 43, a first plug 435 disposed on the lateral plate 34, a first spring 434 disposed between the first block seat 433 and the first plug 435, a first stud 36 fastening the first plug 435 on the lateral plate 34, a second block seat 533 disposed on the upper guide plate 43, a second plug 535 disposed on the lateral plate 34, a second spring 534 disposed between the second block seat 533 and the second plug 535, a second stud 36 fastening the second plug 535 on the lateral plate 34, a first upper roller 41 disposed in the main frame 11, a second upper roller 42 disposed in the main frame 11 abutting the first upper roller 41, a first lower roller 51 disposed in the main frame 11 beneath the first upper roller 41, a second lower roller 52 disposed in the main frame 11 abutting the first lower roller 51 and beneath the second upper roller 42, a first upper shaft 411 extending from the first upper roller 41, a first upper driven gear 37 connected to a first end of the first upper shaft 411, a second upper shaft 421 extending from the second upper roller 42, a second upper driven gear 38 connected to a first end of the second upper shaft 421, a first lower shaft 511 extending from the first lower roller 51, a first lower driven gear 37a connected to a first end of the first lower shaft 511, a second lower shaft 521 extending from the second lower roller 52, a second lower driven gear 38a connected to a first end of the second lower shaft 521, the first upper driven gear 37 engaging with the follower gear 31, the second upper driven gear 38 engaging with the first upper driven gear 37, the first lower driven gear 37a engaging with the follower gear 31, and the second lower driven gear 38a engaging with the first lower driven gear 37a.

Referring to FIG. 5 again, a net 6 is disposed between the first upper driven gear 37 and the first lower driven gear 37a and disposed between the second upper driven gear 38 and the second lower driven gear 38a.

Figure 8:
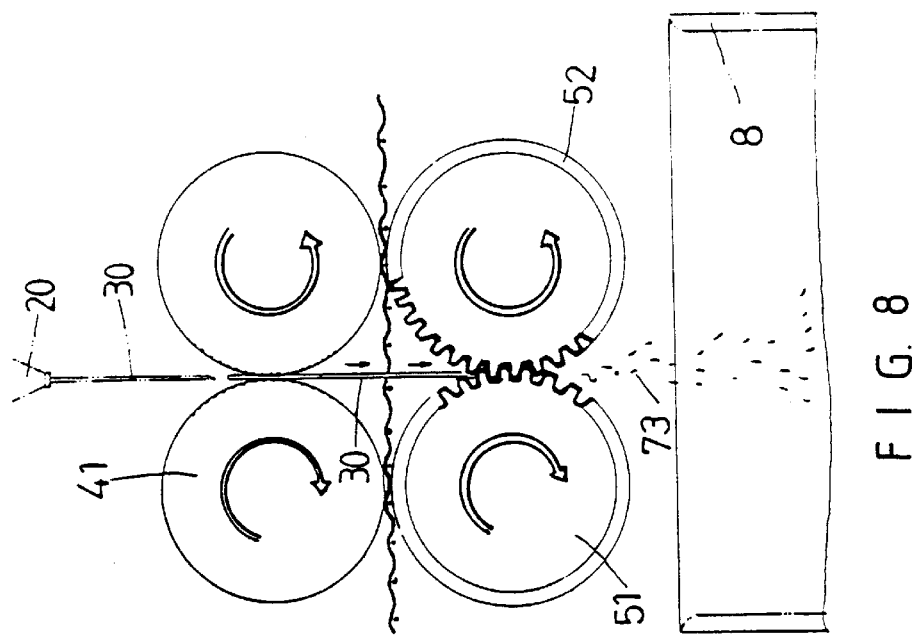
FIG. 8 is a schematic view illustrating an operation of a needle destruction device of a preferred embodiment in accordance with the present invention.
Figure 7:
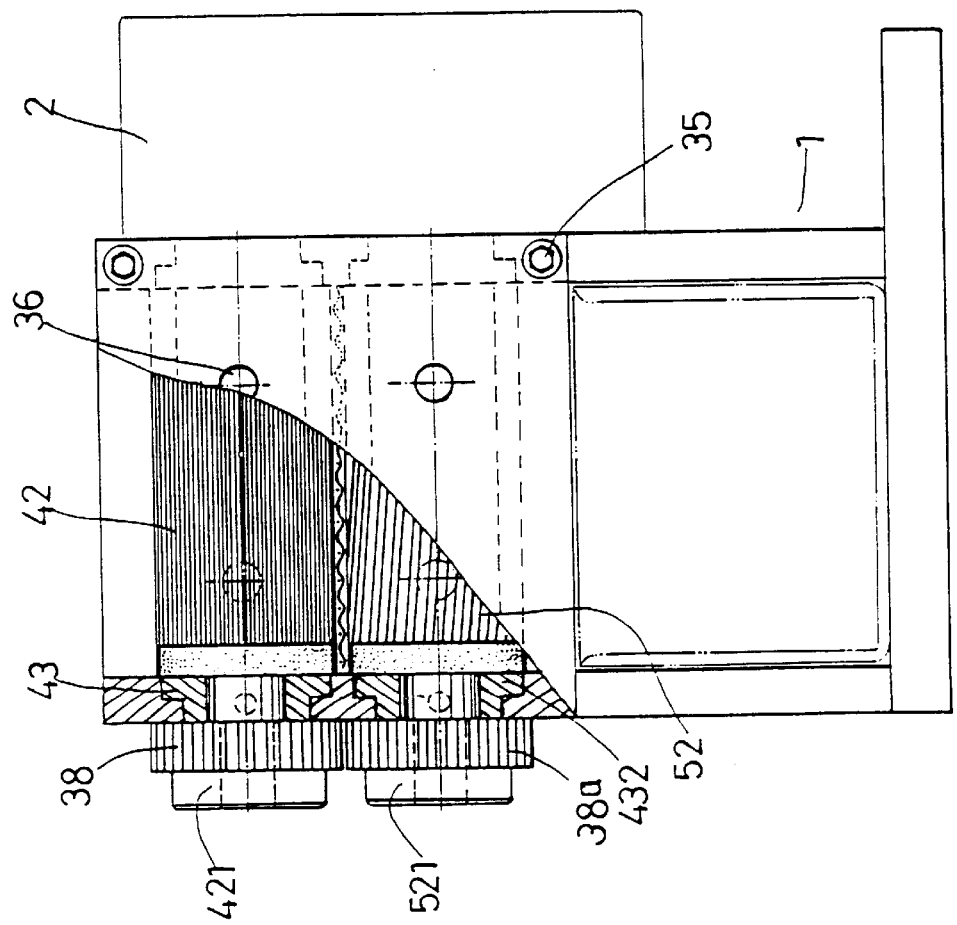
FIG. 7 is another elevational view of a needle destruction device of a preferred embodiment in accordance with the present invention.

Referring to FIG. 8, the needle device is placed between the first upper roller 41 and the second upper roller 42. The needle cannula 30 and the needle hub 20 pass through a spacing between the first upper roller 41 and the second upper roller 42, the net 6, and another spacing between the second lower shaft 521 and the second lower roller 52. Therefore, the needle device is cut into pieces 73.

The invention is not limited to the above embodiment but various modification thereof may be made. Further, various changes in form and detail may be made without departing from the scope of the invention.

I claim:

1. A needle destruction device comprises:

a main frame, a lateral plate disposed on the main frame, a motor disposed on the main frame, a motor shaft extending from the motor, a drive gear connected to a first end of the motor shaft, a follower gear engaging with the drive gear, an upper guide plate disposed in the main frame, a lower guide plate disposed in the main frame and beneath the upper guide plate, an upper slot defined between the upper guide plate and the main frame, a lower slot defined between the lower guide plate and the main frame, a first block seat disposed on the upper guide plate, a first plug disposed on the lateral plate, a first spring disposed between the first block seat and the first plug, a first stud fastening the first plug on the lateral plate, a second block seat disposed on the upper guide plate, a second plug disposed on the lateral plate, a second spring disposed between the second block seat and the second plug, a second stud fastening the second plug on the lateral plate, a first upper roller disposed in the main frame, a second, upper roller disposed in the main frame abutting the first upper roller, a first lower roller disposed in the main frame beneath the first upper roller, a second lower roller disposed in the main frame abutting the first lower roller and beneath the second upper roller, a first upper shaft extending from the first upper roller, a first upper driven gear connected to a first end of the first upper shaft, a second upper shaft extending from the second upper roller, a second upper driven gear connected to a first end of the second upper shaft, a first lower shaft extending from the first lower roller, a first lower driven gear connected to a first end of the first lower shaft, a second lower shaft extending from the second lower roller, a second lower driven gear connected to a first end of the second lower shaft, the first upper driven gear engaging with the follower gear, the second upper driven gear engaging with the first upper driven gear, the first lower driven gear engaging with the follower gear, and the second lower driven gear engaging with the first lower driven gear.

2. A needle destruction device as claimed in claim 1, wherein a net is disposed between the first upper driven gear and the first lower driven gear and is disposed between the second upper driven gear and the second lower driven gear.

* * * * *